US007886990B2

(12) United States Patent
Scheer

(10) Patent No.: US 7,886,990 B2
(45) Date of Patent: Feb. 15, 2011

(54) ATOMIZING DEVICE WITH PRECISELY ALIGNED LIQUID TUBE AND METHOD OF MANUFACTURE

(76) Inventor: Ingo Werner Scheer, 6455 La Jolla Blvd., La Jolla, CA (US) 92037

( * ) Notice: Subject to any disclaimer, the term of this patent is extended or adjusted under 35 U.S.C. 154(b) by 1148 days.

(21) Appl. No.: 11/408,421

(22) Filed: Apr. 21, 2006

(65) Prior Publication Data

US 2008/0237372 A1 Oct. 2, 2008

Related U.S. Application Data

(60) Provisional application No. 60/674,005, filed on Apr. 22, 2005.

(51) Int. Cl.

| | |
|---|---|
| ***A62C 5/02*** | (2006.01) |
| ***B05B 1/28*** | (2006.01) |
| ***B05B 7/06*** | (2006.01) |
| ***B05B 5/00*** | (2006.01) |
| ***A61M 11/02*** | (2006.01) |
| ***F23D 11/32*** | (2006.01) |

(52) U.S. Cl. ........................... 239/8; 239/290; 239/371; 239/424; 239/690; 239/690.1

(58) Field of Classification Search ..................... 239/8, 239/290, 371, 417, 418, 419, 423, 424, 424.5, 239/425, 434.5, 690, 690.1, 704, 706; 219/121.47, 219/121.51; 174/59

See application file for complete search history.

(56) References Cited

U.S. PATENT DOCUMENTS

| | | | | |
|---|---|---|---|---|
| 4,376,514 | A | 3/1983 | Coffee | |
| 4,964,568 | A | 10/1990 | Rotolico | |
| 5,184,776 | A | 2/1993 | Minier | |
| 5,188,290 | A * | 2/1993 | Gebauer et al. | 239/3 |
| 5,685,482 | A * | 11/1997 | Sickles | 239/3 |
| 5,707,010 | A * | 1/1998 | Manfre et al. | 239/296 |
| 5,868,322 | A * | 2/1999 | Loucks et al. | 239/418 |
| 6,010,084 | A | 1/2000 | Yoshida | |
| 6,012,647 | A * | 1/2000 | Ruta et al. | 239/132.1 |
| 6,032,876 | A * | 3/2000 | Bertsch et al. | 239/418 |
| 6,056,213 | A * | 5/2000 | Ruta et al. | 239/337 |
| 6,142,457 | A | 11/2000 | Holtan | |
| 6,147,347 | A * | 11/2000 | Hirabayashi et al. | 250/288 |
| 6,234,402 | B1 | 5/2001 | Ganan-Calvo | |
| 7,141,788 | B2 * | 11/2006 | Hirabayashi et al. | 250/288 |

OTHER PUBLICATIONS

U.S. Appl. No. 60/615,169, filed Oct. 1, 2004, Scheer, Ingo.

* cited by examiner

*Primary Examiner*—Len Tran
*Assistant Examiner*—Ryan Reis

(57) ABSTRACT

An atomizing device, comprising a fine liquid tube, a holder to permanently fix the tube proximate to its exit end and an optional cap to homogeneously and repeatably disintegrate small liquid amounts is disclosed. A manufacturing method for reproducibly machining the atomizer assembly of the present invention is provided.

14 Claims, 10 Drawing Sheets

ATOMIZING DEVICE WITH PRECISELY ALIGNED LIQUID TUBE AND METHOD OF MANUFACTURE

CROSS-REFERENCE TO RELATED APPLICATIONS

This application relates to and claims priority from commonly owned U.S. Provisional Application Ser. No. 60/674,005, filed on Apr. 22, 2005, which is incorporated herein by reference.

FEDERALLY SPONSORED RESEARCH

Not Applicable

SEQUENCE LISTING OR PROGRAM

Not Applicable

BACKGROUND OF THE INVENTION

1. Field of Invention

The present invention relates to an atomizing device comprising a fine tube as fluid path and its method of manufacture for providing a repeatable performance in terms of droplet size and spatial droplet distribution. The invention is particularly suitable for coating medical devices and for creating fine aerosols.

2. Background of the Invention

Atomizing devices comprising a fine liquid tube as fluid line are used in various applications, such as medical nebulizers, chemical analysis of liquid samples and coating devices to atomize small amounts of liquids.

FIG. 1 depicts an enlarged view of the front section of an exemplary atomizer known by the prior art comprising an inner liquid delivery tube and a support member to secure the liquid delivery tube. A cap may be provided at the exit end of the liquid tube to form an annular gap 106 between the inner liquid delivery tube and the cap surrounding the liquid tube. The support member includes a central bore, having an internal diameter larger than the outside diameter of tube 104, for aligning the liquid tube. Additional points for alignment of the liquid tube (not shown) may be provided by central bores disposed within the support member having slightly larger diameters than the outside diameter of the tube.

The liquid tube may be additionally secured by various mechanisms, such as compression fittings as described in U.S. Pat. App. No. US2005/0029442, collet type connections as described in U.S. Pat. No. 6,337,480 or brace like support structure as provided by U.S. Pat. Nos. 5,868,322 and 6,032,876.

Optimum atomization and particle transport efficiencies generally depends on the spatial characteristics of the spray plume and on the droplet size which, in turn, depends on the shape of the atomizer tip and/or on the roundness and concentricity of the annular gap. This is particularly true, when an atomizing gas is provided through a comparatively small annular gap.

However, with current atomizers there is relatively poor control over the concentricity between the tube support member assembly and the cap for the atomizing gas, resulting in a misalignment of liquid tube relative to cap. A stable and secure support of the liquid tube may not be ensured because the tube is generally not sufficiently supported proximate to the liquid exit. Mechanisms used to support the liquid tube are often connections that don't ensure precise and repeatable positioning of the liquid tube in relation to the cap due to assembly tolerances. For example, tolerances between the outside diameter of tube 104 and inside diameter of bore 103, and tolerances between the location shoulder and cap, as shown in FIG. 1, may lead to an increased error in concentricity between the liquid tube and cap. In U.S. Pat. Nos. 5,868,322 and 6,032,876 an atomizing device is provided having an outer tube comprising a brace-like support structure for mechanically securing the inner liquid tube. However, precise concentricity of the liquid tube and outer tube may not be ensured due to assembly tolerances and possible imperfections of the inner and/or outer tube. In addition, the brace-like support structure comprises gas channels, which may cause constrictions within the flow path. Thus, turbulence in the gas flow may be produced resulting in an unstable flow field and inconsistent spray performance. Furthermore, the gas channels, which are disposed along the micro tube, constitute limitations for generating a flow field with an angular momentum, which may be desirable to improve the atomization process.

Another drawback of conventional atomizers, which usually comprise premanufacturered liquid tubes, are imperfections of the tube in terms of roundness and surface quality as well as manufacturing limitations. Due to the relatively small outside diameter and long length of such liquid tubes it may be difficult or even not possible to compensate such imperfections by machining the tip region. To overcome given quality limitations of prefabricated liquid tubes and maximize concentricity it is desirable to machine or even shape the tip of the liquid tube, which is particularly beneficial in electrostatic spraying applications. In addition, there is a risk of misalignment of the liquid tube in relation to the cap when disassembling and reassembling the tube support member assembly during cleaning and maintenance operations, which may result in poor spray performance.

It has been furthermore found that when pneumatic assisted atomizers are used, comprising a very fine liquid tube that is not sufficiently stabilized towards the atomizing end, the spray performance may change during the same spray run. Gas stream 105, as depicted in FIG. 1, which exits the annular gap and surrounds the liquid tube, may have an impact on position and alignment of the liquid tube in relation to the gas orifice. Depending on operating conditions and atomizer configuration, the gas flow may cause the liquid tube to oscillate and change its position during operation, resulting in an inconsistent spray performance of the atomizer over time.

Imperfections of the tube tip and/or in the annular region directly translate into an inhomogeneous spray pattern, a relatively wide size range of droplets and increased droplet sizes. In addition, the shape and surface quality of the atomizing end at the liquid exit may influence the droplet break up and may result in poor efficiency of the atomization process, particularly in the case of electrostatic atomization. The spray performance of pneumatic atomizers, in terms of symmetric spatial particle distribution and tight droplet size distribution, is closely related to the roundness and concentricity of the annular gap. Any imperfection and eccentricity between the axes of the liquid delivery tube and the cap can cause the flow of the atomizing gas to be cylindrically asymmetric with respect to the axis of the liquid exiting from the liquid delivery tube. Hence, inhomogeneous gas velocities within the annular gap will lead to nebulization by the atomizing gas that is different on different sides of the spray plume.

Poor spray stability and droplets that are too large and polydisperse in size may result in poor reproducibility and often poor stability during operation which, in turn, may lead to coating defects or reduced sample analysis efficiency.

OBJECT OF THE INVENTION

Accordingly, there is a need for an atomizing device that overcomes the aforementioned problems with the prior art and provides improved stability and reproducibility of precision spraying processes.

One object is to provide an atomizing device comprising a tube holder assembly, wherein the liquid tube is permanently fixed within the holder proximate to the exit end of the liquid tube, and the error of concentricity between the fine liquid tube and holder is compensated by a final machining operation.

Yet another object is to modify the shape of the liquid tube holder assembly, particularly of the tip of the liquid tube, to compensate imperfections of the liquid tube for improved atomizer performance.

Another object is to provide an pneumatic atomizing device, comprising a tube holder assembly and cap, that ensures the concentric alignment of the tube in relation to the cap to reproducibly generate a uniform spray pattern and small droplets with a tight droplet distribution.

Still another object is to provide an atomizing device having a flow path with minimum perturbation of the atomizing gas flow to generate a stable flow field and to achieve a consistent atomization.

Another object is to provide a atomizing device having a compact and robust design that can be manufactured reproducibly, resulting in a repeatable performance from one atomizer to the next.

A further object is to allow easy assembling and disassembling without the risk of misalignment of the air cap relative to the liquid tube.

Yet another object is to provide a manufacturing method for machining the atomizer assembly, which allows shaping of the tip of the liquid tube and results in improved concentricity, roundness and surface quality.

These and additional features and advantages of the invention will be more readily apparent upon reading the following description of exemplary embodiment of the invention and upon reference to the accompanying drawings herein.

SUMMARY

In one embodiment of the present invention, a device for disintegrating a liquid into fine droplets is provided, comprising at least one fine liquid tube having an outer wall, an entrance end and an exit end, a cap, surrounding and essentially coaxial with the liquid tube, having an exit opening proximal to the exit end of the liquid tube, and a holder with at least one holding section, through which the liquid tube extends. The outer wall of the liquid tube is fixed within the holding section to prevent displacement of the liquid tube in any direction orthogonal to the holding section axis and to allow machining of the liquid tube holder assembly. At least a portion of the liquid tube and at least a portion of the holder are machined in order to compensate the error of concentricity between the axis of the liquid tube and the axis of the holder. The cap is connected to the machined portion of the holder to provide an annular intermediate space between the liquid tube holder assembly and cap. The annular intermediate space has at least one gas inlet feeding directly into it and at least one exit opening and is free of intermediate structures. In one or more embodiments, the gas inlet may be positioned such that a gas flow field with an angular momentum can be generated. The exit opening of the cap may be manufactured by internal turning to improve roundness. The machining operation of the holder and liquid tube assembly may be performed in one setting. The machining operation of the holder and liquid tube assembly may be performed by turning, using the same finishing cut for the holder and tube. The liquid tube can be permanently fixed within the holding section. The holding section may be disposed proximal to the exit end of the liquid tube. The atomizing device may additionally comprise means for forming an electric field at the exit end.

In a further embodiment, a device for disintegrating a liquid into fine droplets is provided, comprising at least one fine liquid tube having an outer wall, an entrance end and an exit end, a holder with at least one holding section through which the liquid tube extends, and means for forming an electric field at the exit end to disintegrate the liquid. The outer wall of the liquid tube is fixed within the holding section to prevent displacement of the liquid tube in any direction orthogonal to the holding section axis and to allow machining of the liquid tube holder assembly. At least a portion of the liquid tube and at least a portion of the holder are machined in order to compensate the error of concentricity between the axis of the liquid tube and the axis of the holder. In one or more embodiments, the machining operation of the liquid tube holder assembly may be performed in one setting. The tube may be permanently fixed within the holding section. The exit end of the liquid tube may be machined so that the tip diameter is reduced and shaped in order to improve the performance of the device. The machining operation of the liquid tube holder assembly may be performed by turning, using the same finishing cut for holder and liquid tube. The liquid tube may be additionally secured and coupled to the electrical means through a compression fitting.

In certain embodiments, a method for machining a device for disintegrating a liquid into fine droplets is provided, including a fine liquid tube having an outer wall, an entrance end and an exit end and a holder having at least one holding section for the liquid tube. This method comprises the steps of connecting the liquid tube to the holder so that the outer wall of the liquid tube is fixed within the holding section to allow machining of the liquid tube holder assembly, and machining the holder tube assembly so that at least a portion of the liquid tube and at least a portion of the holder are machined to compensate the error of concentricity between the axis of the liquid tube and the axis of the holder. In one embodiment, the cutting operation of the liquid tube holder assembly may be performed by turning, using the same finishing cut for liquid tube and holder.

In still another embodiment, a method for machining a device for disintegrating a liquid into fine droplets is provided, including a fine liquid tube having an outer wall, an entrance end and an exit end and a holder having at least one holding section for the liquid tube. This method comprises the steps of machining the holding section for the liquid tube by internal turning, wherein at least a portion of the final holder shape is machined in the same setup, and connecting the liquid tube to the holder so that the outer wall of the liquid tube is fixed within the holding section and the liquid tube is located at a predetermined position in relation to the holder.

DRAWINGS

The accompanying drawings, which are incorporated in and constitute a part of this specification, serve to explain the principles of the invention. The drawings are in simplified form and not to precise scale.

BRIEF DESCRIPTION OF THE DRAWINGS/PREFERRED EMBODIMENTS

The invention provides a compact atomizing device for reproducibly forming droplets from a liquid with improved operational stability, reliability and reproducibility compared to prior art atomizing devices. The atomizer is designed to allow precise and repeatable machining of the liquid tube holder assembly according to the manufacturing procedure described later herein. The liquid tube is embedded in a holding section between the liquid tube and the surrounding holder, and is disposed towards the exit end to provide support for the liquid tube resulting in minimum perturbation of the atomizing gas flow. Broadly, the invention provides an atomizer comprised of at least one liquid tube holder unit, the liquid tube permanently embedded in the holder proximate to the liquid exit end. The liquid tube and holder are positioned in a concentric arrangement about a common central axis and the tube is secured in a centered position. In one or more embodiments, the invention further provides a cap which, when coupled with the liquid tube holder unit, provides a conduit for the atomizing gas. The cap may be removably secured by a thread and aligned through a centering section between the holder and cap, so that a concentric alignment between the liquid tube and the cap as well as repeatable assembly and disassembly can be provided.

DETAILED DESCRIPTION

While the invention will be described in connection with certain embodiments, it will be understood that the invention is not limited to these embodiments. On the contrary, the invention includes all alternatives, modifications and equivalents as may be included within the spirit and scope of the present invention. Details in the Specification and Drawings are provided to understand the inventive principles and embodiments described herein, to the extent that would be needed by one skilled in the art to implement those principles and embodiments in particular applications that are covered by the scope of the claims.

Figure 2:
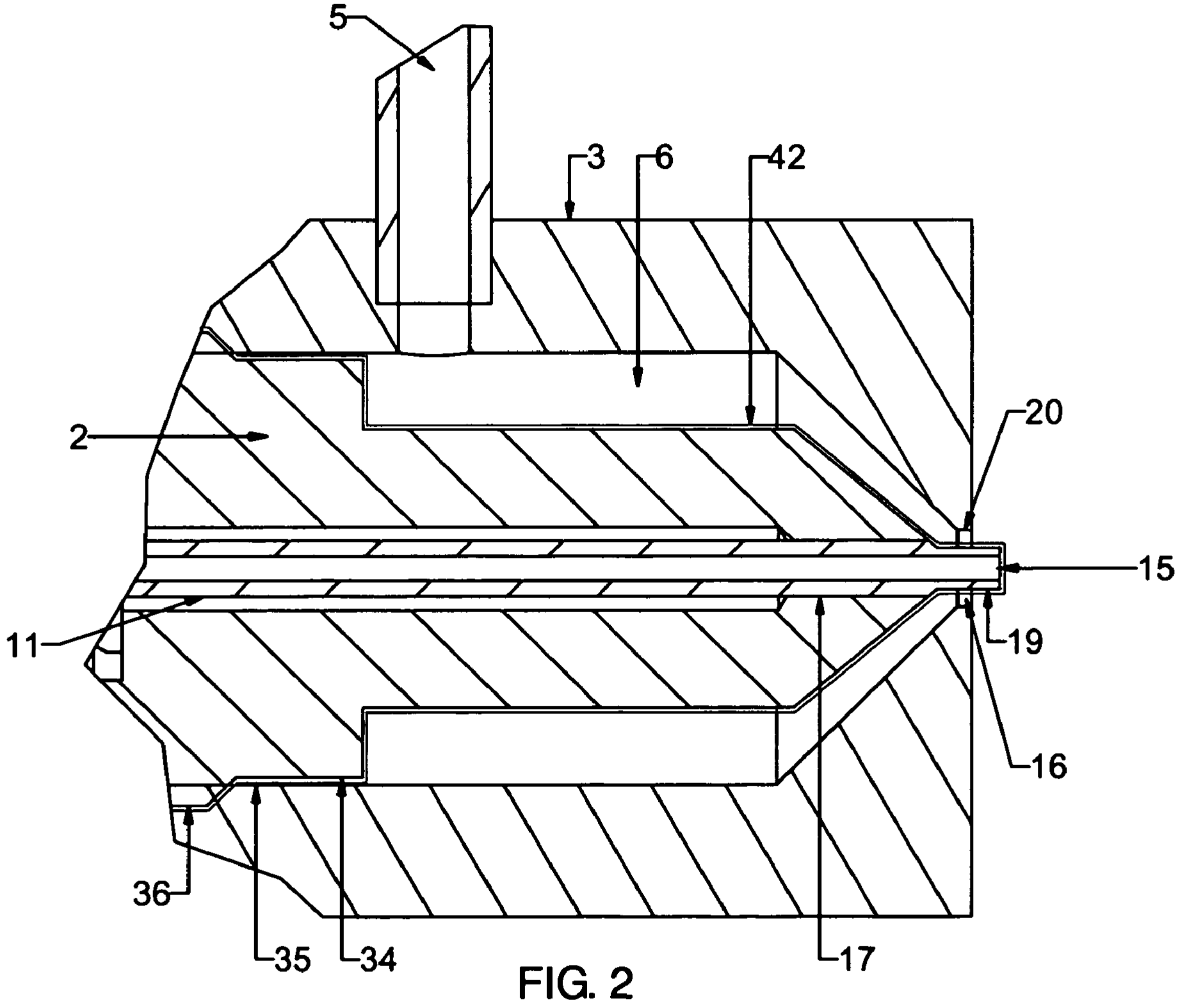
FIG. 2 is a longitudinal cross-sectional view of the front portion of the atomizer of the present invention.

FIG. 2 illustrates the front section of the atomizer of the present invention comprising liquid tube 11, cap 3 and holder 2, which is used to align the cap in relation to the tube. The holder is preferably made from stainless steel or from a polymeric material, such as polyetheretherketone (PEEK). The tube can be constructed from any material which is impervious to chemical attack by the solution to be sprayed and which allows machining by cutting. The tube is preferably made from stainless steel or from a polymeric material. The outside diameter of the tube may range between approximately 0.3 and 1.615 mm depending on the particular application. All dimensions used herein are suggestive and not intended to be restrictive. In this embodiment, liquid tube 11 extends axially within holder 2 to a position slightly beyond air cap 3. Alternatively, the liquid tube may be flush with the cap or may be placed at a recessed position with respect to the cap. Tube 11 is permanently connected to support holder 2 by joint 17. Joint 17 is disposed next to the atomizing end of tube 11 and secures tube 11 along its entire perimeter. The axis of the tip of tube 19 is concentric with the axis of location shoulder 34 for cap 3. Cap 3 is aligned with location shoulder 34, which locates the axis of the tube holder assembly to be concentric with the axis of cap 3. Thus, air cap 3 can be easily removed for maintenance and cleaning of the atomizer without the risk of misalignment. Cap 3 is secured to the liquid tube holder assembly by thread 36 and a small annular gap 16 to permit passage of gas is provided. The tip diameter of tube 19 and cap orifice diameter 20 define the width of the annular gap. The holder secures the tube in a centered position and allows finish machining of the assembly and shaping of the tip of the tiny tube. For precise concentricity between the tube and holder, the tip of liquid tube 19 and the outside shape of the holder are machined in one setting, preferably by a turning operation. The contour of the machined section is illustrated by line 42. The final machining operation of the tube holder assembly compensates errors in concentricity. Hence, a proper and stable alignment of tube 11 in relation to location shoulder 34 of holder 2 can be ensured. Besides the concentricity, the roundness of orifice 20 of cap 3 and the tip of liquid tube 19 are crucial for the uniformity and repeatability of the atomization process. For optimized roundness, orifice 20 of air cap 3 and tip of liquid tube 19 are preferably machined using a precision turning operation.

In operation, the liquid is fed at the liquid inlet, while the atomizing gas is fed in gas inlet 5, located in the cap, and flows through gas passage 6 defined by the intermediate space between the tube holder assembly and cap to the exit end aperture and exits the atomizer at the annular gap formed between the liquid tube and the cap orifice. The atomizing gas disintegrates the liquid when it exits the liquid orifice. The liquid and gas are mixed outside the atomizer to obtain an aerosol.

By providing a secure connection and optimized alignment between tube 11 and holder 2 and by machining the assembly, the concentricity between the axis of liquid tube 19 and orifice 20 of cap 3 can be substantially optimized compared to prior art atomizers. Consequently, the annular flow of the atomizing gas is very uniform about the spray axis, resulting in a symmetrical spray pattern.

Figure 3:
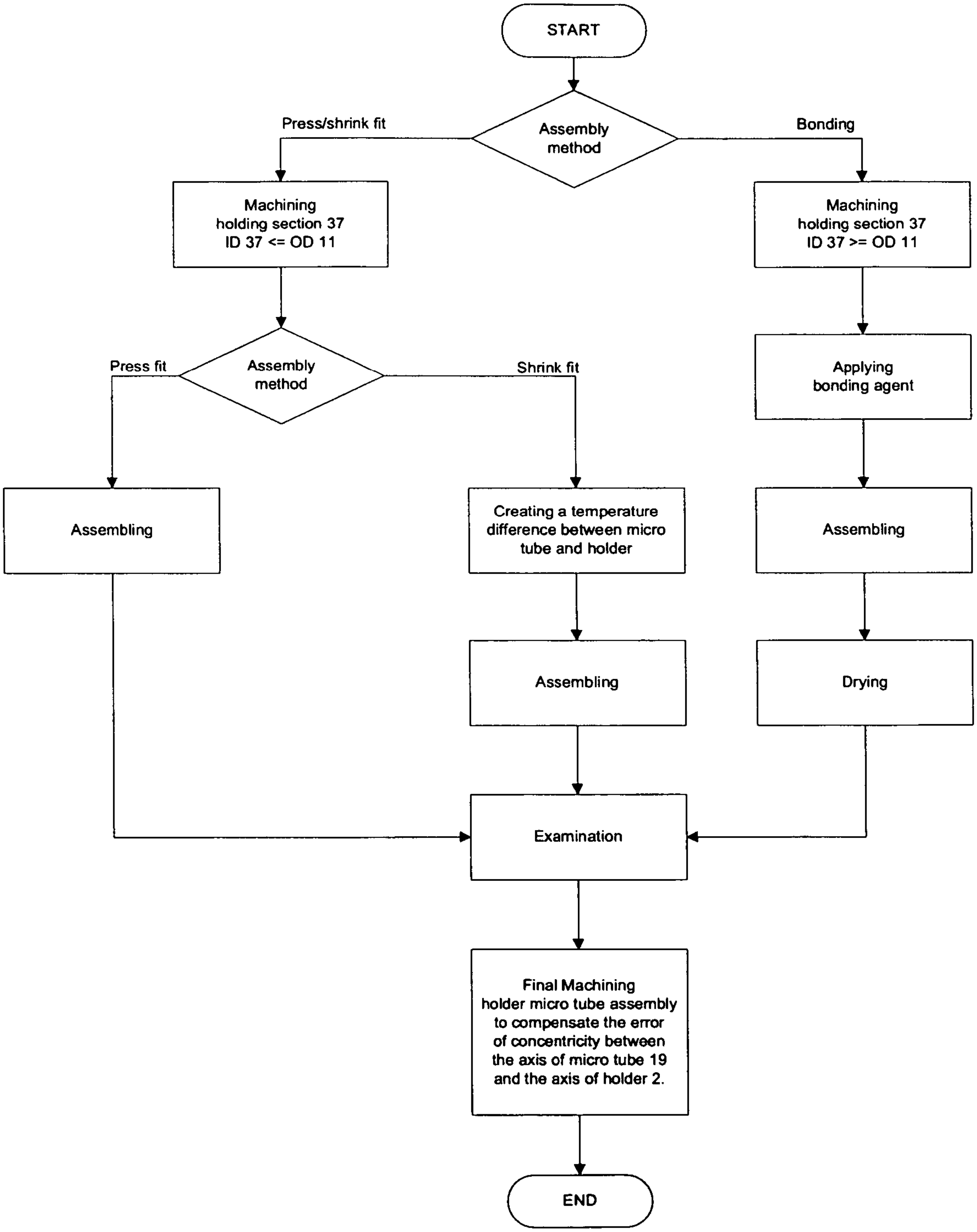
FIG. 3 is a diagrammatic representation of a manufacturing procedure for machining a tube holder assembly comprising a final machining operation.
Figure 4A:
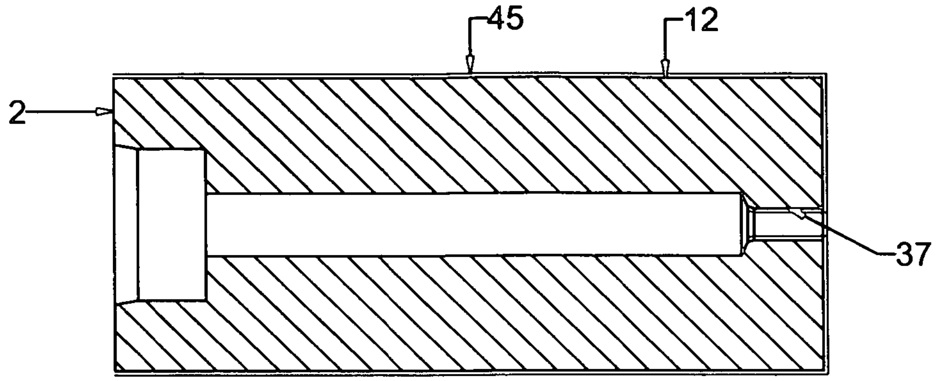
FIG. 4A is a longitudinal cross-sectional view of a holder having a holding section for the liquid tube.
Figure 4B:
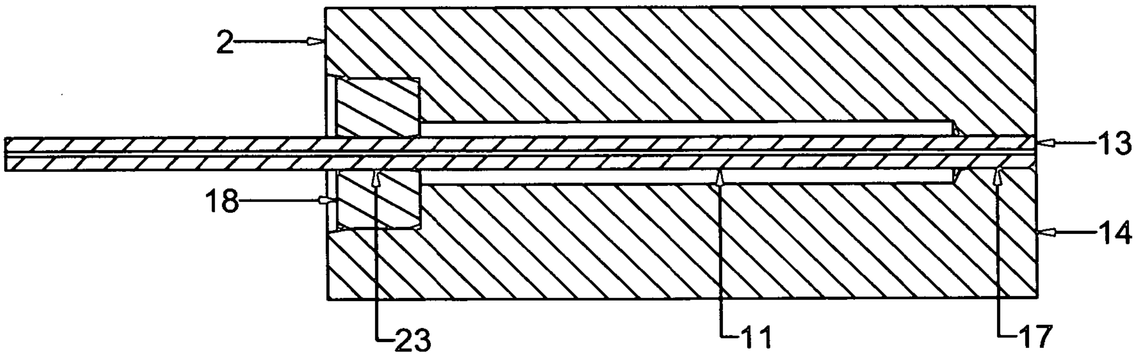
FIG. 4B is a longitudinal cross-sectional view of a tube holder assembly before machining.
Figure 4C:
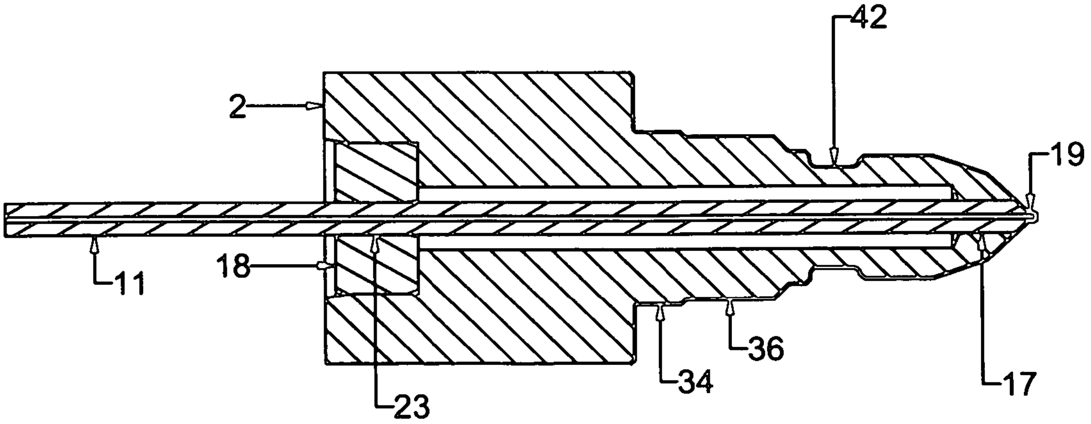
FIG. 4C is a longitudinal cross-sectional view of a tube holder assembly after machining.

To compensate for alignment errors between the liquid tube and holder and to obtain improved roundness of the tube tip, a manufacturing procedure as diagrammatically shown in FIG. 3 and illustrated in FIGS. 4A-C may be adopted.

Referring to FIG. 4A, holder 2 may be manufactured from a solid rod. For best alignment, centering or holding section 37 and holder outside diameter 12 are preferably machined in the same setting by turning using a precision lathe. Internal turning is preferred for centering section 37 because there is a minimized risk of out-of-roundness compared to other machining operations such as drilling. Depending on the size of liquid tube 11, centering section 37 may have a diameter of approximately 0.3 to 2 mm and a length ranging from 2 to 6 mm. In a next step shown in FIG. 4B, liquid tube 11 is mounted within holder 2. To ensure a stable connection between holder 2 and liquid tube 11, at least one permanent joint is provided between the holder and the tube. Additional joints may also be provided for improved stability of the tube and to facilitate machining of the assembly. For example, member 18 may secure the tube at the liquid inlet end resulting in permanent joint 23, which may be obtained through press or shrink fit or by using an adhesive. Alternatively, a removable connection, such as a compression fitting, can be used to obtain a non-permanent joint. Depending on the size and material of liquid tube 11, permanent joint 17 between holder 2 and liquid tube 11, which secures liquid tube 11 along its entire perimeter, can be obtained as described below. If joint 17 is obtained by a press or shrink fit connection, the diameter of centering section 37 is machined slightly smaller than the outside diameter of liquid tube 11. Holder 2 may be heated and liquid tube 11 cooled down to create a temperature difference between both parts. Then, tube 11 is pressed into holder 2 until face 13 of liquid tube 11 and face 14 of holder 2 flush. Alternatively, a permanent joint may be obtained by bonding liquid tube 11 to holder 2. After machining the internal diameter of holder 2 slightly larger than the outside diameter of liquid tube 11, a thin film of adhesive can be applied to the outside surface of liquid tube 11 and/or to centering section 37 to secure liquid tube 11 to holder 2. Then liquid tube 11 can be disposed within the holder so that face 13 of liquid tube 11 and face 14 of holder 2 flush. FIG. 4C depicts machined section 42 of the liquid tube holder unit after a final machining operation. Machined section 42 may extend from the center of liquid tube tip 19 to the outside cylindrical surface of holder 2 and may comprise location shoulder 34 and threaded section 36 for alignment and connection of the cap. The final machining operation compensates possible imperfections of premanufactured liquid tubes and allows shaping of the tip to customize the atomizing device for the particular application.

Figure 5A:
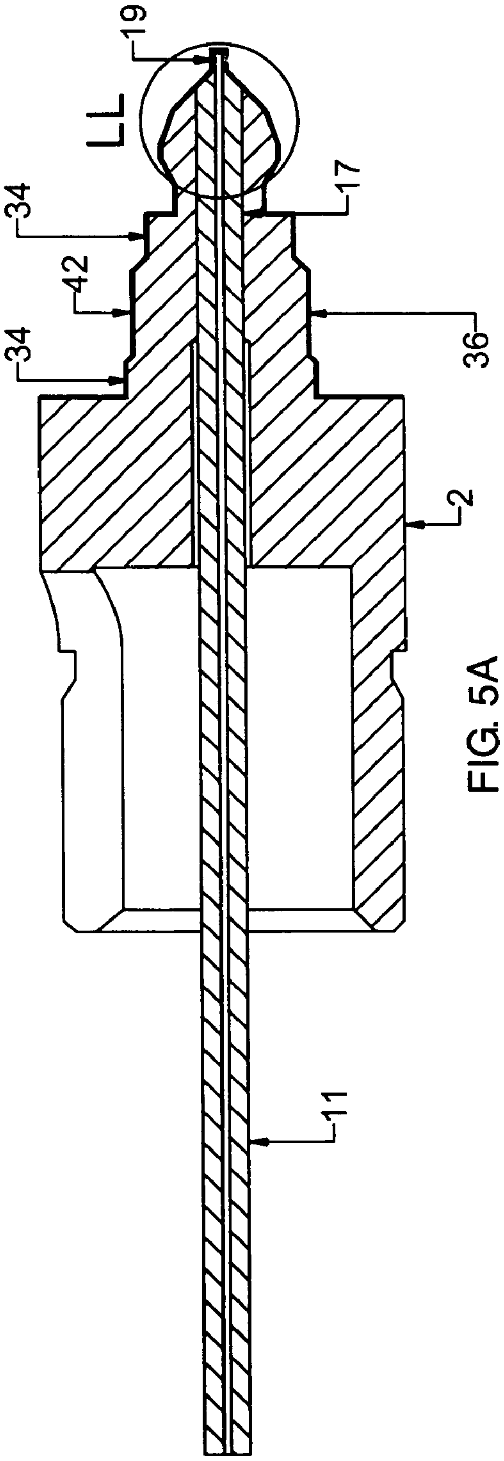
FIG. 5A is a longitudinal cross-sectional view of a atomizer (tube holder assembly) without cap
Figure 5B:
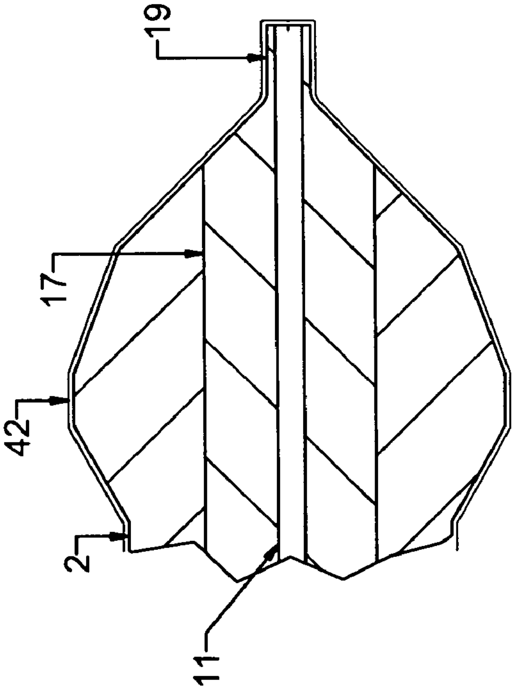
FIG. 5B is an expanded view of the tip region of the atomizer shown in FIG. 5A.
Figure 6A:
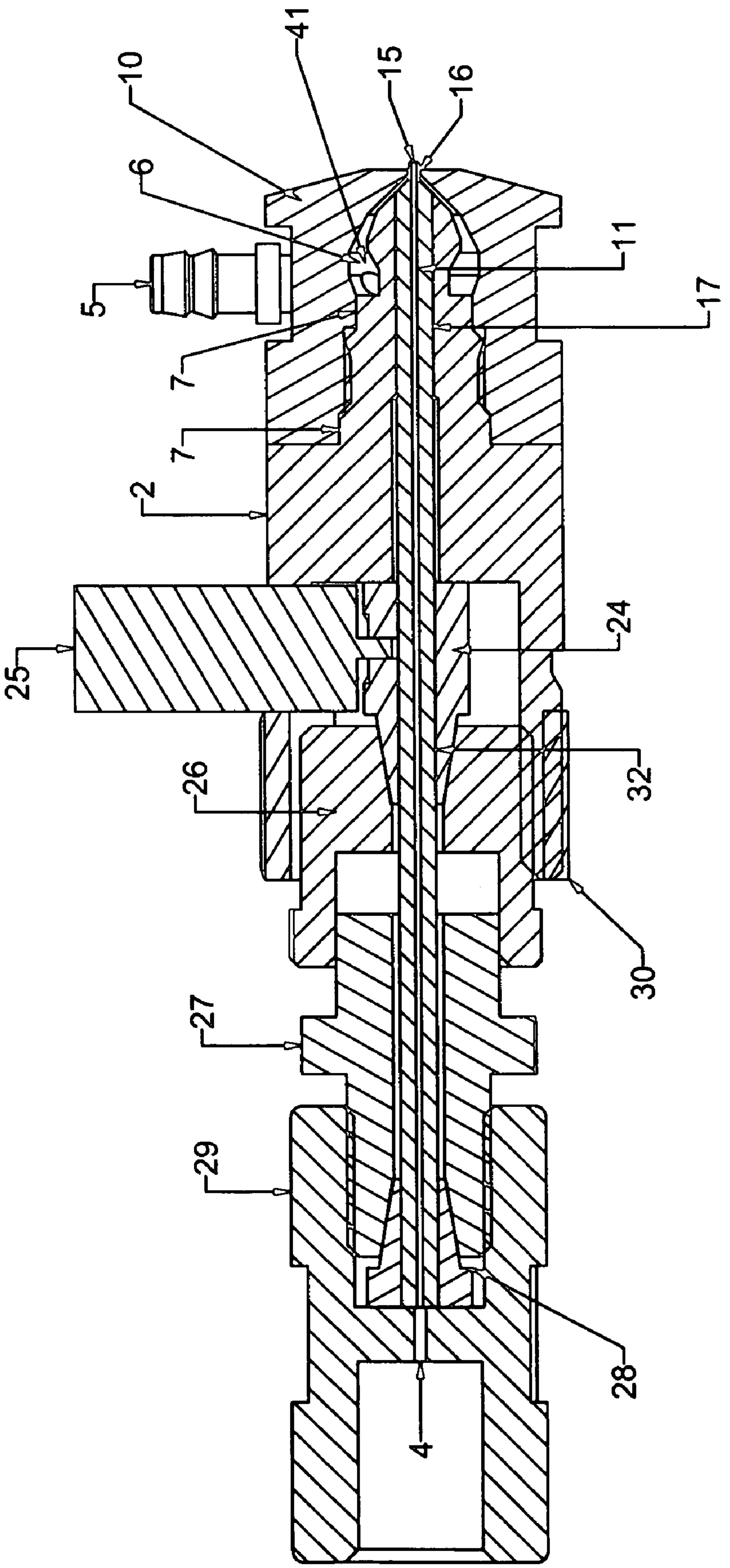
FIG. 6A is a longitudinal cross-sectional view of an atomizer comprising a cap and a connection to a high voltage source.
Figure 6B:
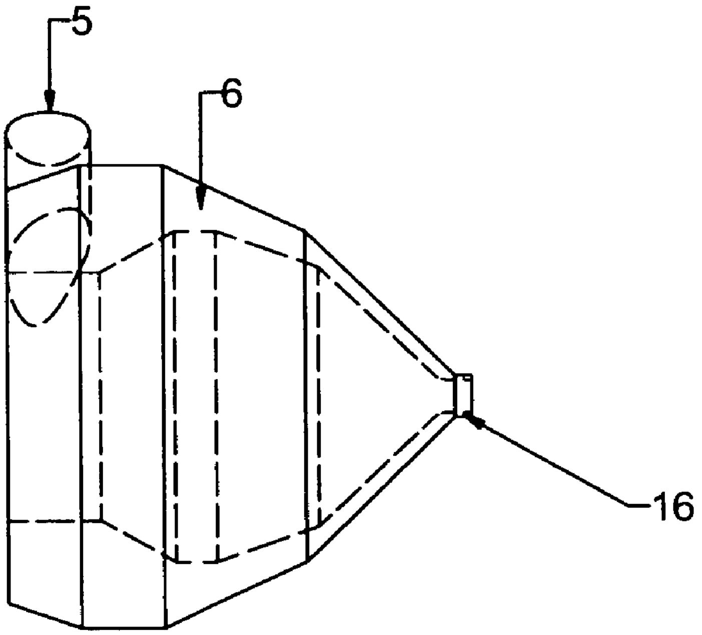
FIG. 6B is a longitudinal expanded view of the gas passage defined by the intermediate space between tube holder assembly and cap.
Figure 6C:
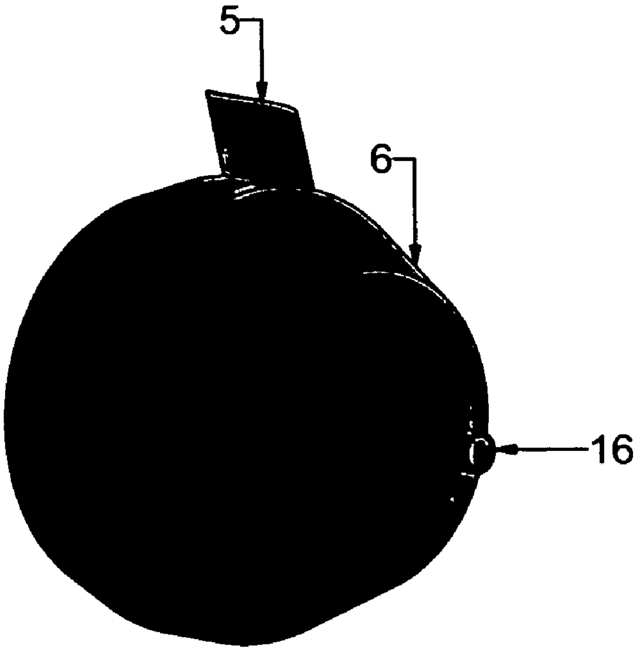
FIG. 6C is a 3-D view of the gas passage defined by the intermediate space between tube holder assembly and cap.

The final machining operation of the tube holder unit of the atomizer, described later herein in FIG. 6, is illustrated in more detail in FIGS. 5A and B. FIG. 5B is an enlarged view of the tube holder unit having machined section 42, which extends to a tapered portion towards the exit end of tube 11. To facilitate machining of centering section 37 and to improve stability of the tube holder unit, a stainless steel tube with a relatively large outside diameter resulting in an enlarged holding section may by used. For example, when a tube with an outside diameter of 1/16 inch, an inside diameter of approximately 0.2 mm and a length of 2 inches (commercially available from Upchurch Scientific, Oak Harbor, USA) is used, a holding section with a comparatively long length of approximately 6 mm can be provided. The holder can be made from a polymeric material such as polyetheretherketone (PEEK). The tube holder unit is preferably machined by turning. The resulting machined section 42, extends from atomizer tip 19 to the cylindrical outer surface of the holder and comprises two centering sections 34 and a threaded section 36 to mount the cap. The tip of the tube has a decreasing outside diameter towards the liquid orifice. Liquid tube 11 and holder 2 are machined using the same finishing cut, resulting in a smooth transition between the tapered section of liquid tube 11 and the tapered section of holder 2. The tapered section of the tube holder assembly is precision machined to obtain a smooth shape and an impingement angle for the atomizing gas resulting in an unobstructed gas flow for improved effectiveness of the atomization process. In addition, a possible error of concentricity between the axis of liquid tube tip 19 and the axis of the machined outer shape of the holder can be compensated.

By providing an atomizer designed to allow machining of the liquid tube holder unit, a superior quality of the annular gap in terms of concentricity, roundness and smooth finish can be obtained. In addition, a facilitated, repeatable and cost-effective manufacturing method for the tube holder unit and especially for the tip of the tube is provided.

FIG. 6A illustrates an exemplary atomizer according to the present invention comprising holder 2, tapered liquid tube 11, and optional cap 10. The liquid tube holder unit is designed to compensate the errors in concentricity between tip 19 of liquid tube 11 and holder 2 and to provide superior roundness of the shaped tube. The liquid tube holder unit is machined according to the manufacturing procedure described in FIG. 4 and FIG. 5. Tube 11 is made from stainless steel and holder 2 and cap 10 are fabricated from a dielectric material, polyetheretherketone (PEEK), polytetrafluoroethylene (PTFE, or Teflon), and the like. Tube 11 is permanently fixed into holder 2 to facilitate subsequent machining of the tube holder assembly. For improved alignment of cap 10 in relation to holder 2, two centering sections 7 having different outside diameters are provided. Liquid tube 11 is connected to holder 2 via permanent joint 17 obtained by press fit and via a compression fitting including ferrule 24 and nut 26. The compression fitting is used to secure the tube and to couple the tube to a high voltage source via cable 25. Union 29, which is connected to tube 11 by an additional compression fitting comprising nut 27 and ferrule 28, provides the liquid inlet port.

FIG. 6B shows gas passage 6 defined by the intermediate space between the tube holder assembly and cap, which is free of intermediate structures and has a decreasing cross-section area towards annular gap 16. In operation, the atomizing gas is introduced at tangential gas inlet 5 and flows towards annular gap 16 provided between the cap and tube holder assembly. A gas flow with an angular momentum is generated, resulting in a flow field with axial and radial velocity components and increased shear forces at the atomizer orifice. The liquid flows through the liquid tube to the atomizing end and is broken up by the atomizing air into very fine droplets having a tight particle size distribution. The break up length of the liquid can be reduced by generating an angular momentum resulting in an improved atomization. In addition, gas passage 6 is designed to minimize turbulence and to produce a stable gas flow, thereby ensuring a consistent atomization of the liquid to be sprayed.

Figure 7:
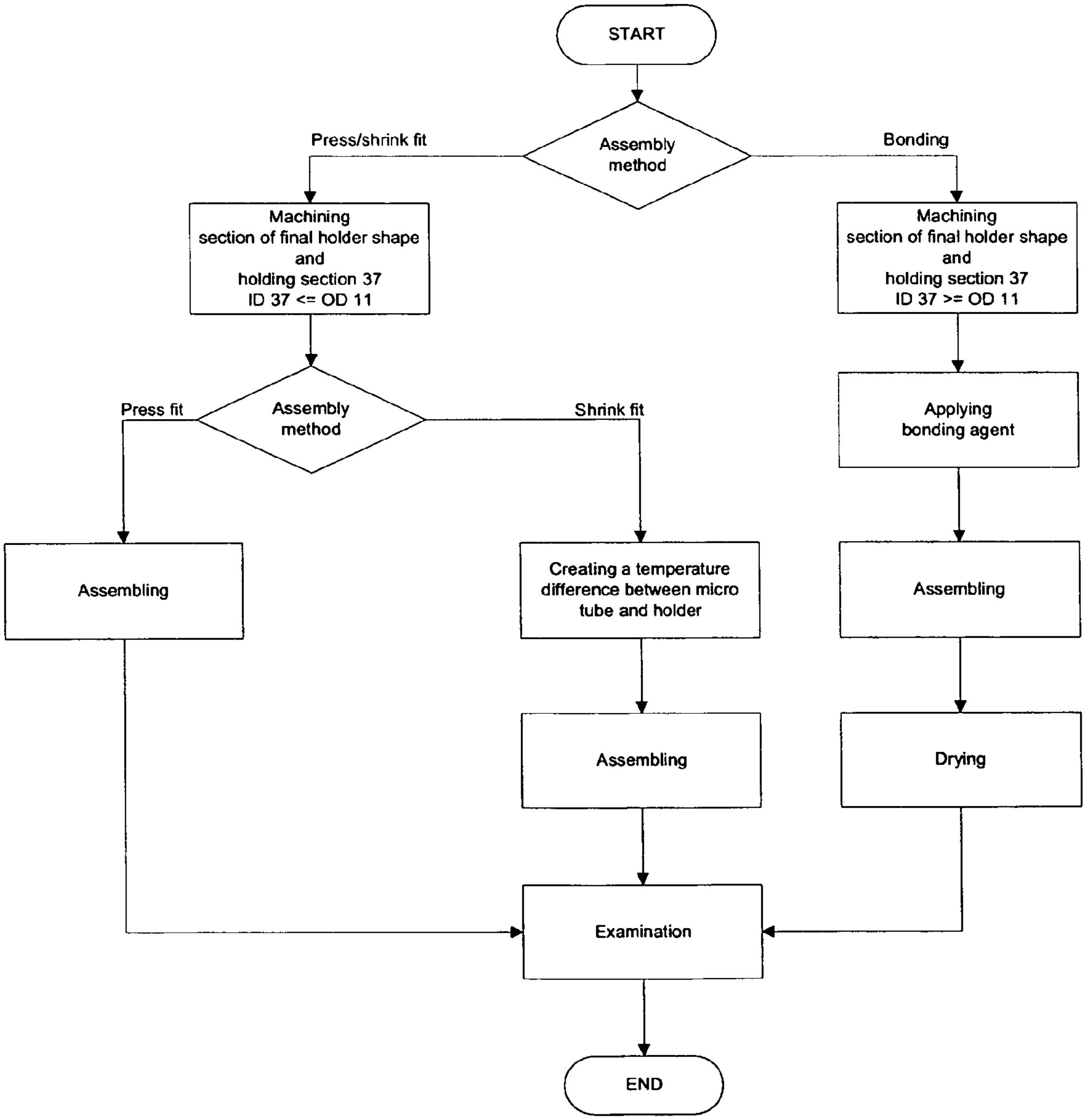
FIG. 7 is a diagrammatic representation of a manufacturing procedure for machining a tube holder assembly.
Figure 8A:
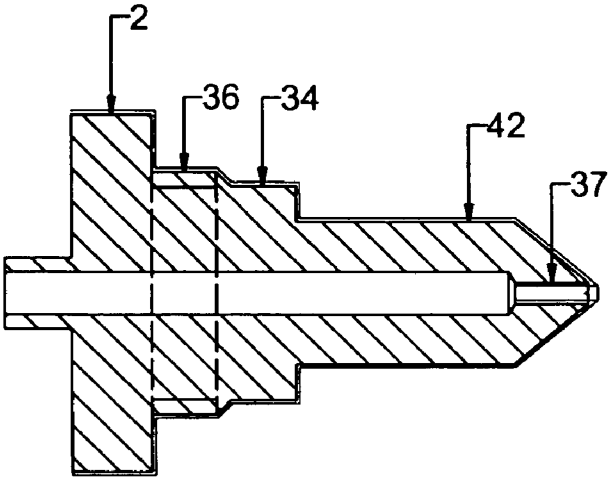
FIG. 8A is a longitudinal cross-sectional view of a holder comprising a holding section for the liquid tube.
Figure 8B:
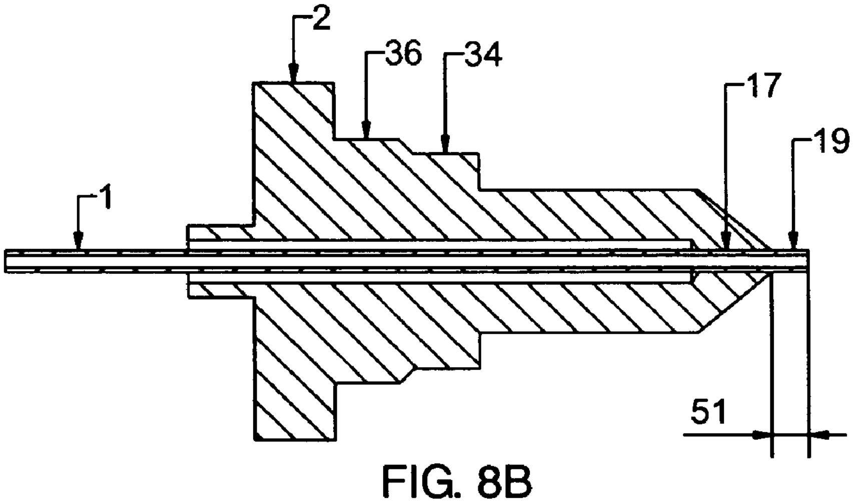
FIG. 8B is a longitudinal cross-sectional view of a tube holder assembly.
Figure 8C:
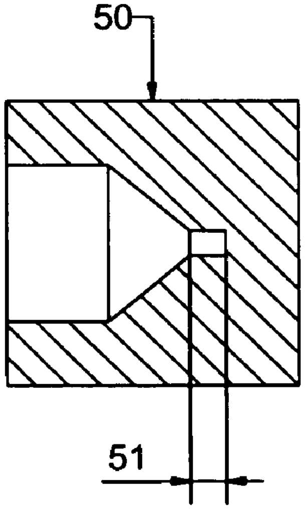
FIG. 8C is a longitudinal cross-sectional view of a mounting fixture.

In the presence of an electrical field the atomization process can be improved by electrically charging the liquid to a very high voltage as described below. Alternatively, the atomizer may also be used without cap 10 to atomize the liquid using only electrostatic energy. In such situations, centering sections 34 may be used for alignment of the tube holder unit. In operation, a fine spray of charged droplets is produced when the liquid flows from the end of the liquid tube and emerges from orifice 15 of tube 11 in the presence of a high electric field. The electric field causes a disruption of the liquid surface and charged liquid droplets are generated. Depending on the polarity of the electric field, positively or negatively charged droplets are produced. The formation of an electrospray plume depends mainly on the electric field distribution in the space proximal to exit end 19 of tube 11, which, in turn, depends on the shape of the electrically conductive surfaces bordering this space. To enhance the electric field gradient in the space proximal to the face of exit end 19 and to improve the atomization, the edge face of exit end 19 may be shaped as a cone by 'sharpening' the end. Depending on the particular operating conditions it may also be formed as a blunt face When using a liquid tube made from a non-machinable material, such as a ceramic material or fused silica, the manufacturing procedure diagrammatically shown in FIG. 7 and illustrated in FIGS. 8A-C is preferably employed. Referring to FIG. 8A, holder 2 comprises location shoulder 34 for the cap and holding section 37 for the liquid tube. The diameter of location shoulder 34 and the inner diameter of liquid tube holder centering section 37 are machined in the same setup to ensure proper alignment of cap 3 in relation to liquid tube 1. Location shoulder 34 for cap 3 is preferably manufactured by external turning and centering section 37 for liquid tube 1 by internal turning. In order to achieve an optimized concentricity, an internal turning operation is preferred compared to drilling and reaming. As shown in FIG. 8B, holder 2 and liquid tube 1 are precisely aligned and fixed by a permanent joint. Depending on the material and size of the liquid tube a permanent joint may be obtained by shrink fit, press fit or bonding. For a shrink or press fit connection, the internal centering diameter of centering section 37 is machined slightly smaller than the outside diameter of liquid tube 1. Holder 2 may be heated until its internal centering diameter is larger than the outside diameter of liquid tube 1 to obtain a shrink fit connection. In a next step, liquid tube 1 is placed into holder 2 at a predefined distance from holder tip. Alternatively, a permanent joint may be obtained by bonding liquid tube 1 to holder 2. The internal diameter of centering section 37 of holder 2 is machined slightly larger than the outside diameter of liquid tube 1 and a thin film of adhesive is applied to the outside surface of liquid tube 1 to secure it to holder 2. To ensure a repeatable and precise positioning of the liquid tube in relation to the holder tip a mounting fixture, such as illustrated in FIG. 8C, may be used to assemble liquid tube and holder.

Figure 1:
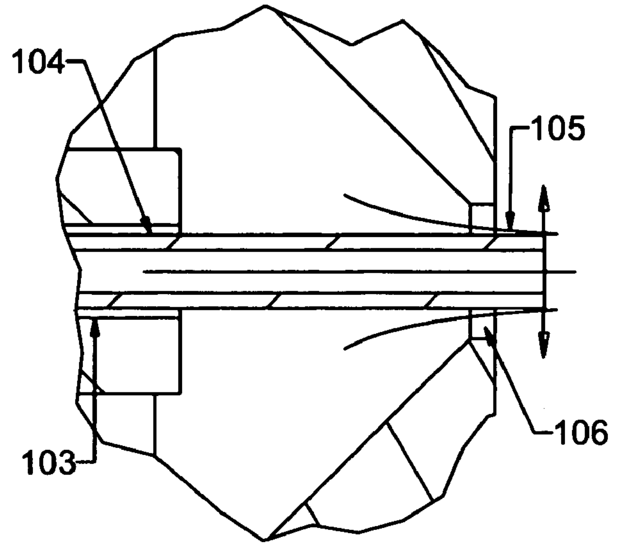
FIG. 1 PRIOR ART
FIG. 1 (Prior Art) is a longitudinal cross-sectional view of the front portion of a conventional atomizer.

In order to demonstrate the performance of the atomizing device of the present invention various spray tests have been conducted. The spatial droplet distribution and the droplet size distribution have been measured and compared to an exemplary atomizer known by the prior art. The atomizers used were pneumatic atomizers having a fine liquid tube with an internal diameter of approximately 0.2 mm. The prior art atomizing device comprises a removable tube secured using a compression fitting. The front section of prior art atomizing device is shown in FIG. 1. The atomizing device of the present invention includes a permanently fixed micro tube, fabricated according to the manufacturing procedure of FIG. 3. The spray pattern was measured 20 mm downstream from the nozzle orifice using an Optical Patternator. The liquid to be atomized (DI Water) was supplied by a syringe pump (manufactured by Hamilton Company, Reno, Nev.) at a flow rate of 15 ml/h and the gas (air) was fed at a pressure of 0.7 bar.

Figure 9:
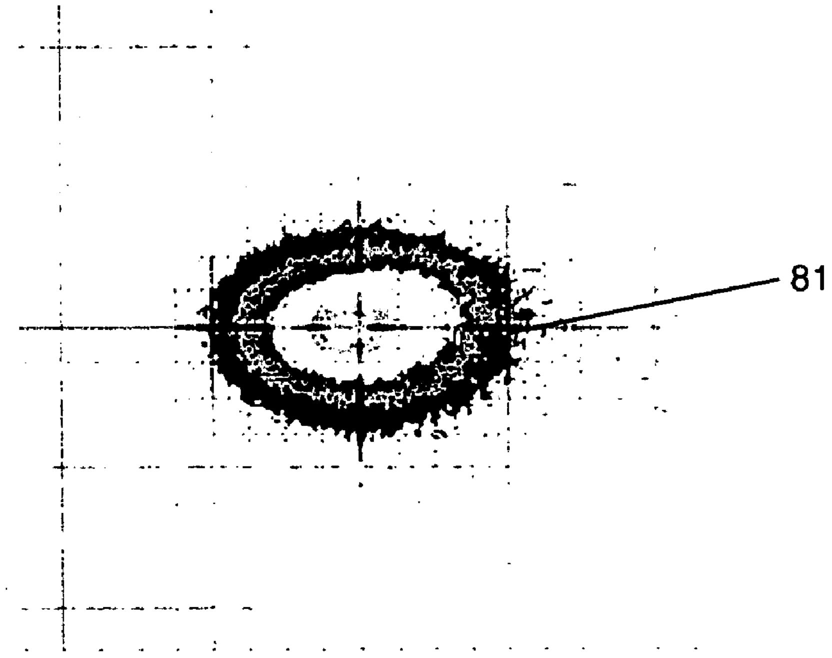
FIG. 9 (Prior Art) is a spatial droplet distribution generated by a conventional atomizer.
Figure 10:
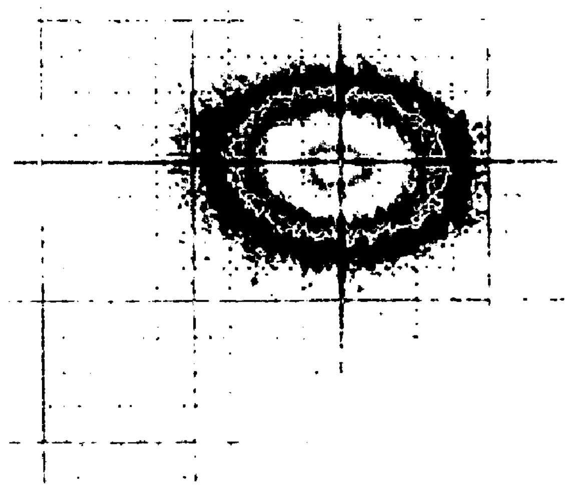
FIG. 10 is a spatial droplet distribution generated by the atomizer of the present invention.

FIG. 9 depicts the spray pattern of the prior art atomizing device. The spray pattern has an asymmetric spray distribution comprising coarse particles in the right portion, depicted by line 81. The asymmetric spray distribution may be caused by inhomogeneous gas velocities within the annular gap resulting from a misalignment of the liquid tube in relation to the cap and/or from poor roundness of the annular gap. In contrast, the spray pattern of the atomizer of the current invention, as shown in FIG. 10, has a homogeneous spatial droplet distribution.

To compare the atomizer performance in terms of atomization consistency, a droplet size analysis has been performed. The droplet sizes of both atomizing devices have been measured using the Helos BF Laser Diffractometer (manufactured by Sympatec, Lawrenceville, USA), which was located 30 mm downstream from the atomizer orifice. The liquid to be sprayed was supplied by a syringe pump (manufactured by Hamilton Company, Reno, Nev.) at a flow rate of 3.5 ml/h and the atomizing gas was fed at a gas pressure of 1.0 bar. Eight measurement runs have been conducted during a spray time of approximately 5 minutes.

Figure 11:
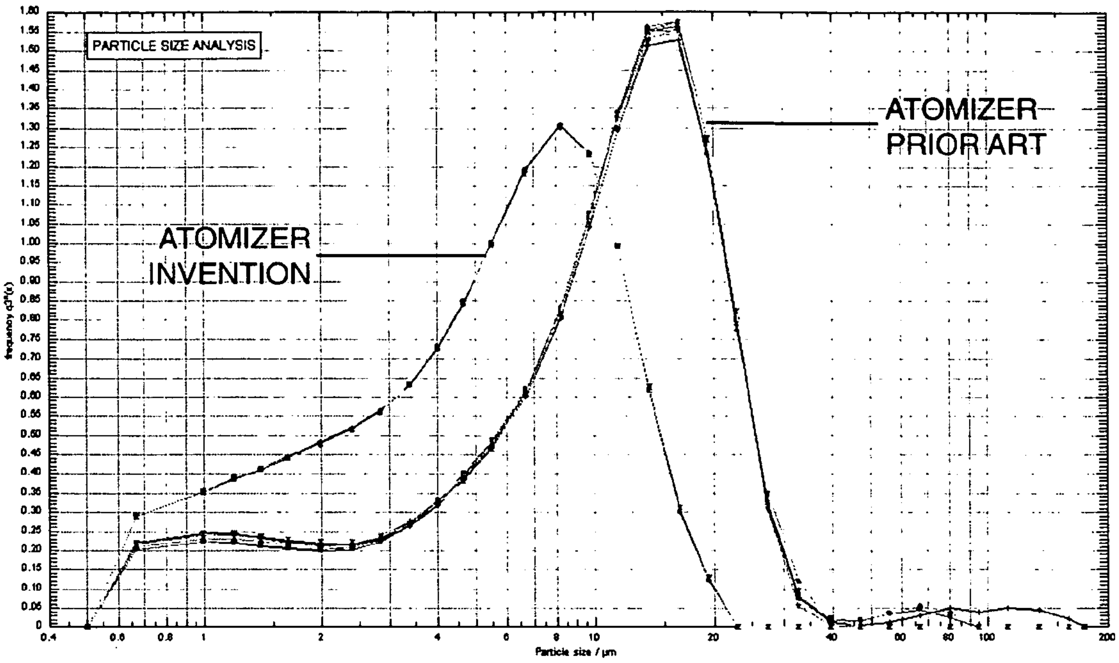
FIG. 11 is a comparison of the droplet size distributions between an atomizer of the Prior Art and of the present invention.

It has been shown, as depicted in FIG. 11, that the prior art atomizing device generates an inconsistent droplet size distribution, in particular for droplet sizes ranging from 0.8 to 4 microns and for droplet sizes of 25 microns or more. Furthermore, comparatively large droplets of 40 microns or more have been detected in four measurement runs. In contrast, the atomizing device of the current invention provides a comparatively homogeneous droplet size distribution during the whole spray run.

Figure 12:
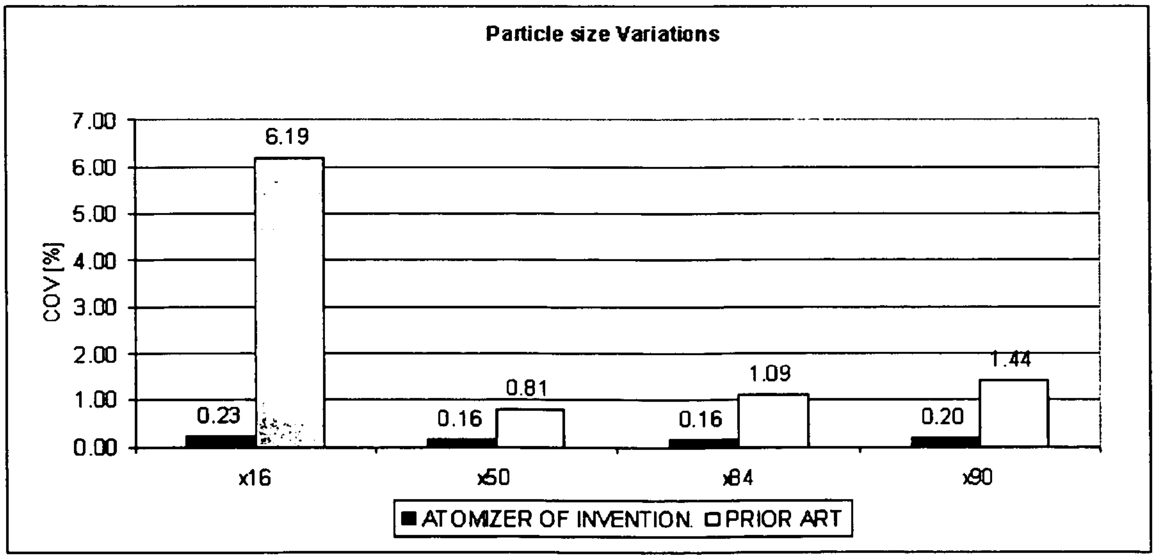
FIG. 12 is a comparison of the COV between an atomizer of the Prior Art and of the present invention.

FIG. 12 illustrates the coefficient of variation (COV) of both atomizers, which can be used as a measure for the spray performance variation over time. The coefficient of variation has been calculated for the ×16, ×50, ×64, ×90 values, shown in the table below, obtained during eight measurement runs for each atomizer.

| | ATOMIZER INVENTION | | | | ATOMIZER PRIOR ART | | | |
|---|---|---|---|---|---|---|---|---|
| RUN | ×16 [μm] | ×50 [μm] | ×84 [μm] | ×90 [μm] | ×16 [μm] | ×50 [μm] | ×84 [μm] | ×90 [μm] |
| 1 | 1.52 | 5.45 | 10.42 | 11.98 | 2.99 | 11.18 | 19 | 21.25 |
| 2 | 1.53 | 5.46 | 10.45 | 12.02 | 2.93 | 11.09 | 18.75 | 20.89 |
| 3 | 1.52 | 5.45 | 10.42 | 11.98 | 2.75 | 10.97 | 18.65 | 20.83 |
| 4 | 1.52 | 5.46 | 10.44 | 12 | 2.63 | 11.11 | 19 | 21.25 |
| 5 | 1.52 | 5.46 | 10.44 | 12 | 2.58 | 10.93 | 18.52 | 20.63 |
| 6 | 1.52 | 5.46 | 10.46 | 12.04 | 2.6 | 10.95 | 18.71 | 20.9 |
| 7 | 1.52 | 5.44 | 10.41 | 11.97 | 2.61 | 11.09 | 19.13 | 21.58 |
| 8 | 1.52 | 5.44 | 10.44 | 12.02 | 2.56 | 11.01 | 18.84 | 20.95 |

Referring to FIG. 12, the COV values of the atomizer of the present invention are significantly smaller than the values obtained for the prior art atomizing device. The repeatable spray performance indicates that the liquid atomization has been improved by optimizing the atomization region in terms of concentricity between the liquid tube and annular gap, surface quality and by providing a securing mechanism which prevents misalignment of the liquid tube during operation. The results outline the advantages of the design and manufacturing methodology adopted for the atomizer of the present invention in terms of spray pattern quality and atomization consistency.

The invention claimed is:

1. A device for disintegrating a liquid, comprising at least one fine liquid tube having an outer wall, an entrance end and an exit end, a holder with at least one holding section and a cap surrounding and essentially coaxial with the liquid tube having an exit opening proximal to the exit end of the liquid tube being connected to the holder wherein the liquid tube completely extends through the holder;

the holding section of the holder is proximal to the exit end of the liquid tube and the distance between the liquid tube exit end and the holding section is smaller than three times the diameter of the holding section;

the liquid tube is secured within the holding section to prevent displacement of the liquid tube in any direction orthogonal to the holding section axis;

the liquid tube and a portion of the holder are shaped after assembly to compensate the error of concentricity of the liquid tube holder assembly; and the cap is connected to the holder to provide an intermediate space between liquid tube holder assembly and cap; and wherein the device produces a spray with a substantionally homogeneous spatial droplet distribution and the droplet size variation is less than 0.8%.

2. A device for disintegrating a liquid according to claim 1, wherein at least one gas inlet is positioned so that a gas flow field with an angular momentum can be generated.

3. A device for disintegrating a liquid according to claim 1, wherein the exit opening of the cap is manufactured by internal turning to improve roundness.

4. A device for disintegrating a liquid according to claim 1, wherein the device further comprises means for forming an electric field at the exit end.

5. A device for disintegrating a liquid comprising: at least one fine liquid tube having an outer wall, an entrance end and an exit end, a holder with at least one holding section through which the liquid tube extends, and means to form an electrical field at the exit end to disintegrate the liquid wherein the liquid tube completely extends through the holder;

the holding section of the holder is proximal to the exit end of the liquid tube and the distance between the liquid tube exit end and the holding section is smaller than three times the diameter of the holding section;

the outer wall of the liquid tube is fixed within the holding section to prevent displacement of the liquid tube in any direction orthogonal to the holding section axis; and at least the portion of the liquid tube being located towards the exit end is at least partially shaped by machining to compensate the concentricity error of the liquid tube holder assembly;

whereby a spray with a substantially homogeneous spatial droplet distribution is produced.

6. A device for disintegrating a liquid according to claim 5, wherein a machining operation of the liquid tube and of at least a portion of the holder is performed in the same setting.

7. A device for disintegrating a liquid according to claim 5, wherein the tube is permanently fixed within the holding section.

8. A device for disintegrating a liquid according to claim 5, wherein the liquid tube holder assembly is machined by turning, using the same finishing cut for the holder and liquid tube.

9. A device for disintegrating a liquid according to claim 5, wherein the liquid tube is secured and coupled to the electrical means through a compression fitting.

10. A device according to claim 5, wherein a machining operation comprises the steps of: connecting the liquid tube to the holder so that the outer wall of the liquid tube is fixed within the holding section to allow machining of the liquid tube holder assembly and machining at least a portion of the liquid tube being located in vicinity to the exit end.

11. A device for disintegrating a liquid according to claim 5, further comprising: a cap surrounding and essentially coaxial with the liquid tube having an exit opening proximal to the exit end of the liquid tube and being connected to the holder to provide an intermediate space between liquid tube holder assembly and cap.

12. A method for disintegrating a liquid using a device comprising at least one fine liquid tube having an outer wall, an entrance end and an exit, a holder with at least one holding section through which the liquid tube extends and a cap surrounding and essentially coaxial with the liquid tube, the holding section of the holder being proximal to the exit end of the liquid tube and the distance between the liquid tube exit end and the holding section being smaller than three times the diameter of the holding section, the outer wall of the liquid tube being secured within the holding section to prevent displacement of the liquid tube in any direction orthogonal to the holding section axis, and the cap having an exit opening proximal to the exit end of the liquid tube and being connected to the holder to provide an intermediate space between liquid tube holder assembly and cap, comprising the steps of:

feeding the liquid into the fine liquid tube and compressed gas into the intermediate space;

flowing the gas through the intermediate space so that the gas is expelled in immediate vicinity of the liquid tube; and disintegrating the liquid exiting from the exit end of the liquid tube into a spray having a homogeneous spatial droplet distribution using the aerodynamic forces produced during the expansion of the atomizing gas wherein the droplet size variation is less than 0.8%.

13. The method according to claim 12, wherein 50 percent of the generated droplets have a size smaller than 6 microns.

14. The method according to claim 12, further comprising the step of applying the spray to a medical device to form a coating.

* * * * *